United States Patent [19]

Christiansen et al.

[11] Patent Number: 4,627,273

[45] Date of Patent: Dec. 9, 1986

[54] APPARATUS AND METHOD FOR DETERMINING THE MINIMUM MISCIBILITY PRESSURE OF A GAS IN A LIQUID

[75] Inventors: Richard L. Christiansen; Hiemi Kim, both of Littleton, Colo.

[73] Assignee: Marathon Oil Company, Findlay, Ohio

[21] Appl. No.: 770,819

[22] Filed: Aug. 28, 1985

[51] Int. Cl.⁴ ............................................. G01N 7/00
[52] U.S. Cl. ................................................ 73/61.1 R
[58] Field of Search ................... 73/64.4, 64.2, 61 R, 73/61.1 R, 19

[56] References Cited

U.S. PATENT DOCUMENTS

| | | | |
|---|---|---|---|
| 3,276,844 | 10/1966 | Davison et al. | 23/253 |
| 3,300,385 | 1/1967 | Danon | 167/84.5 |
| 3,854,324 | 12/1974 | Altshuler et al. | 73/64.4 |
| 4,455,860 | 6/1984 | Cullick et al. | 73/19 |

OTHER PUBLICATIONS

W. F. Yellig and R. S. Metcalfe, Determination and Prediction of CO$_2$ Minimum Miscibility Pressures, *J. Pet. Technology,* pp. 160–168, Jan. 1980.

Technical Disclosure Bulletin, vol. XXI, Marathon Oil Company, Findlay, Ohio, p. 13, 1981.

G. C. Wang and E. V. Knight, Visual Study of Miscibility Development of CO$_2$–Crude Systems, 2nd Ass. Rech. Tech.

Exploit Petrol. Enhanced Oil Recovery Europe Symp. (Paris, 82.11.08-10) Proc., pp. 269–278, 1982.

G. C. Wang, Determination of Miscibility Pressure by Direct–Observation Method, DOE/MC/16140-T2, pp. 1–13, 1982.

*Primary Examiner*—Michael J. Tokar
*Assistant Examiner*—Hezron E. Williams
*Attorney, Agent, or Firm*—Jack L. Hummel; Rodney F. Brown

[57] ABSTRACT

An apparatus and method for determining the minimum miscibility pressure of a gas in a liquid comprises injecting a gas bubble into a transparent tube containing the liquid at a fixed predetermined pressure and temperature and observing the bubble behavior as it passes through the liquid in the tube. Thereafter, the pressure is increased and the procedure is repeated until the lowest pressure at which a bubble exhibits characteristic miscibility behavior in the liquid is determined, which is defined as the minimum miscibility pressure.

30 Claims, 5 Drawing Figures

A  B  C

APPARATUS AND METHOD FOR DETERMINING THE MINIMUM MISCIBILITY PRESSURE OF A GAS IN A LIQUID

BACKGROUND OF THE INVENTION

1. Technical Field

The invention relates to an apparatus and method for predetermining the operating pressure of an enhanced oil recovery gas flood and, more particularly, for determining the minimum miscibility pressure of a gas in a liquid.

2. Description of Related Art

The minimum miscibility pressure of a gas in a crude oil is a critical parameter in the operation of gas floods employed as enhanced oil recovery processes. The minimum pressure at which a gas is miscible in the crude oil in place is the basis for optimizing the operating pressure of the gas flood. It is generally preferable to conduct the flood at or slightly above the minimum miscibility pressure (MMP) of the flooding gas in the crude oil because considerably more oil is recovered when the gas is miscible in the oil than when it is immiscible. Furthermore, increasing the pressure substantially above the MMP does not significantly improve oil recovery while exposing the operator to additional operating costs, increased risk of undesirable formation fracturing, and increased safety hazard.

A number of methods and apparatus are known for determining the MMP of a gas in an oil, including the widely accepted slim tube method. A slim tube is a long narrow tube approximately 12.2 to 18.3 meters long and having an inside diameter of 0.64 cm or less and packed with an unconsolidated material such as sand or glass beads. The tube is saturated with oil and thereafter flooded with a gas at constant pressure and temperature. The oil recovery is determined at that pressure and then similar floods are conducted at different pressures. The oil recovery at each pressure is measured as a function of the volume of gas injected. The oil recovery efficiency is determined thereafter as a function of flooding pressure. The MMP, as determined by the slim tube method, is the pressure above which there is very little increase in oil recovery efficiency. The slim tube method is extremely time-consuming, taking several days to determine the MMP of a single gas-crude oil system. See Yellig and Metcalf, "Determination and Prediction of $CO_2$ Minimum Miscibility Pressures," *J. Pet. Tech.*, v. 32 (1980) pp. 160–168.

U.S. Pat. No. 4,455,860 to Cullick et al describes a method for determining the MMP of $CO_2$ which comprises filling a capillary tube with oil and injecting $CO_2$ into the tube at a fixed temperature and pressure to displace the oil. The MMP is calculated from pressure response data.

Direct visual methods have been proposed for determining the MMP of $CO_2$ in crude oil. In Wang and Knight, "Visual Study of Miscibility Development of $CO_2$-Crude Systems," *Proceedings of the European Symposium at Paris*, Nov. 8–10, 1982, pp. 269–278, a $CO_2$-rich vapor phase and a crude oil-rich liquid phase are maintained in a visual cell at a constant temperature and pressure until equilibrium is attained. The pressure is gradually increased and the $CO_2$ is recirculated through the oil, adding additional $CO_2$ as needed, to maintain the pressure until a third $CO_2$-rich liquid phase develops between the first two phases. The pressure is further increased until the interface disappears between the $CO_2$-rich liquid phase and the $CO_2$ vapor phase. This is defined therein as the MMP. A second test is performed to confirm a multiple contact miscibility mechanism. In the second test, a $CO_2$-rich liquid phase and a crude oil liquid phase are present in the cell. Oil droplets are released into the $CO_2$-rich liquid phase at the top of the visual cell. The droplets gradually enrich the $CO_2$-rich liquid phase until the droplets become miscible therein, confirming the multiple contact miscibility mechanism.

Although the direct visual determination of MMP appears to be more straightforward than other known experimental methods, a more rapid and reliable visual method is needed which more closely approximates the multiple contact miscibility mechanism of a miscible gas flood in a formation by a single experimental procedure.

SUMMARY OF THE INVENTION

The present invention relates to a process and apparatus for measuring the MMP of a gas in a liquid. The specific apparatus employed is a rising bubble apparatus (RBA) comprised of a transparent vessel termed a sight gauge, a bubble injection means, and a pressure maintenance means. The sight gauge has a transparent tube mounted therein which contains a liquid of interest and enables visual observation of a gas bubble passing through the liquid.

According to the method of the invention the tube is filled with a liquid sample, such as crude oil. The tube is maintained at a substantially fixed pressure by a hydraulic fluid in the vessel. A gas is injected into the vessel, which forms a bubble at the bottom of the tube. The buoyant force on the bubble causes it to rise up through the oil and the bubble's shape is observed as it rises. After the bubble has passed through the oil and out the top of the tube, the used oil sample is flushed from the tube and replaced with a fresh oil sample having the same composition as the first. A bubble is launched through the fresh oil sample in the same manner as above, but at a pressure incrementally greater than the pressure of the previous run. Additional runs are repeated in the same manner at increasing increments of pressure. The lowest pressure at which the bubble exhibits characteristic multiple contact miscibility behavior in the oil is defined as the MMP.

The present apparatus and method quickly and accurately determine the MMP of any number of gases in liquids. The apparatus and method simultaneously approximate in a single procedure the multiple contact miscibility mechanism believed to occur in an actual subterranean formation. Unlike other known visual methods, the present apparatus and method enables the practitioner to observe the dynamic behavior of the gas in a multiple contact environment as it flows through the liquid. Non-visual slim tube methods produce results comparable to the present method, but are extremely time-consuming.

DESCRIPTION OF THE PREFERRED EMBODIMENTS

The MMP is defined hereafter as the pressure at which the interfacial tension at the interface between a gas bubble and a liquid approaches zero, causing the gas bubble to dissipate in a characteristic manner. At or slightly above the MMP, the gas bubble exhibits a unique and distinguishable behavior in the liquid which enables one to ascertain the MMP. In practice the interfacial tension at the interface between the bubble and the oil is not exactly zero at the MMP because a number of fluid mechanic effects may rupture the bubble before an interfacial tension of exactly zero is reached. However, for practical purposes the sum of the effects are very small relative to the interfacial tension. Thus, an interfacial tension of zero at the MMP is a good approximation.

The liquid in the present case may be any liquid in which the selected gas is at least partially miscible within a predetermined operating pressure range. The liquids include liquid hydrocarbons such as crude oils. Most gases having commercial potential for enhanced oil recovery applications, such as $CO_2$, $N_2$, and $CH_4$, are at best only partially miscible as initially injected into the formation with crude oils at practical operating pressures. An in situ multiple contact miscibility mechanism transforms the gas into one which is substantially completely miscible in the oil. The present apparatus and process approximate gas-oil multiple contacting in the formation.

Figure 1:
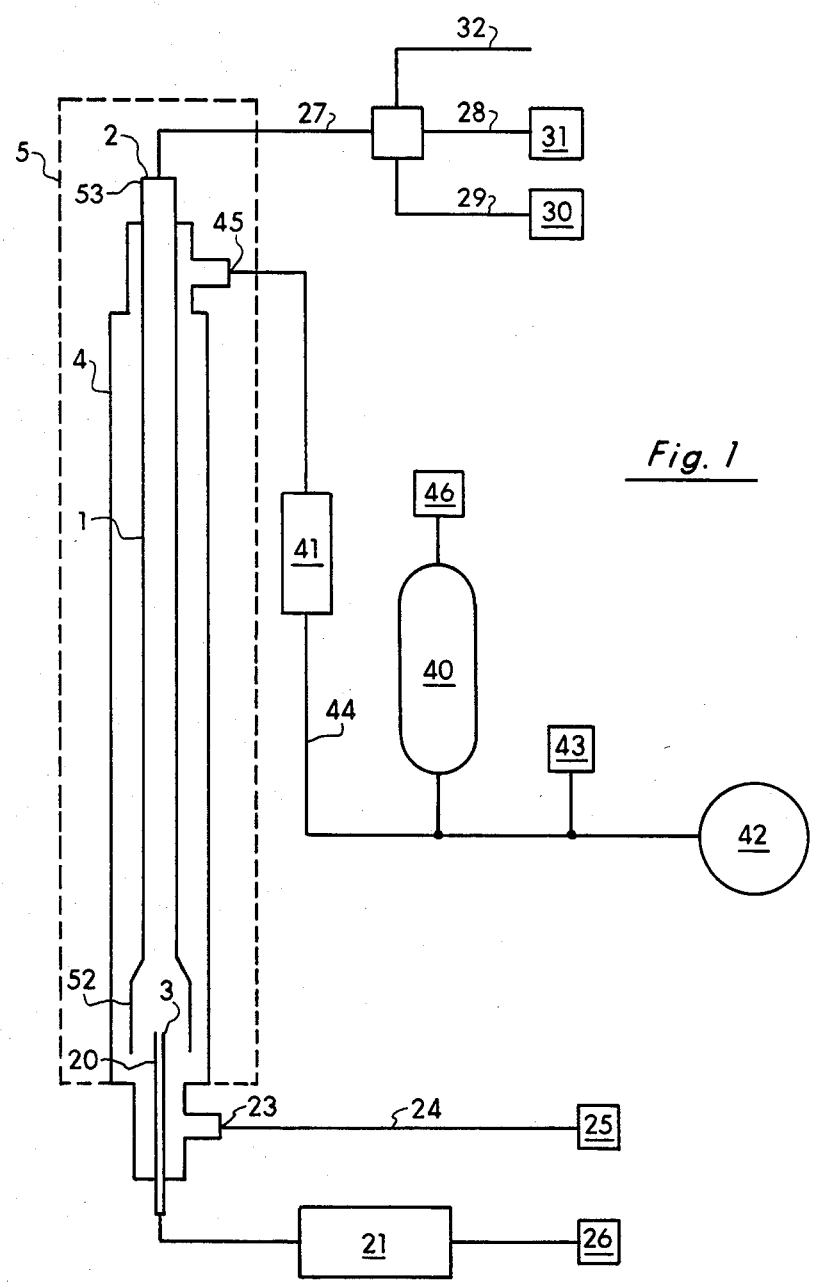
FIG. 1 is a schematic drawing of the rising bubble apparatus.

The rising bubble apparatus (RBA) shown in FIG. 1 is comprised of a transparent tube 1 mounted in a transparent high pressure vessel 4 termed a sight gauge. Tube 1 has a longitudinal axis perpendicular to its cross-section. Tube 1 is mounted such that the longitudinal axis deviates from the horizontal at an angle greater than 0° up to about 90°. The geometry of the tube cross-section is not critical, but the cross-sectional area of the tube must be sufficiently large to enable a visible bubble to pass through it. At the same time the depth of the cross-section is limited by the opacity of the liquid therein. For example, the maximum cross-sectional depth at which a bubble is visible in a dark crude oil is about 1 mm. Thus, a tube having an elongated cross-section substantially wider than it is deep is preferred for viewing relatively opaque liquids such as dark crude oils. This configuration maximizes the cross-sectional area while minimizing the depth of the tube. Examples of such cross-sections include rectangles, ovals, ellipses, and the like.

Figures 2, 3:
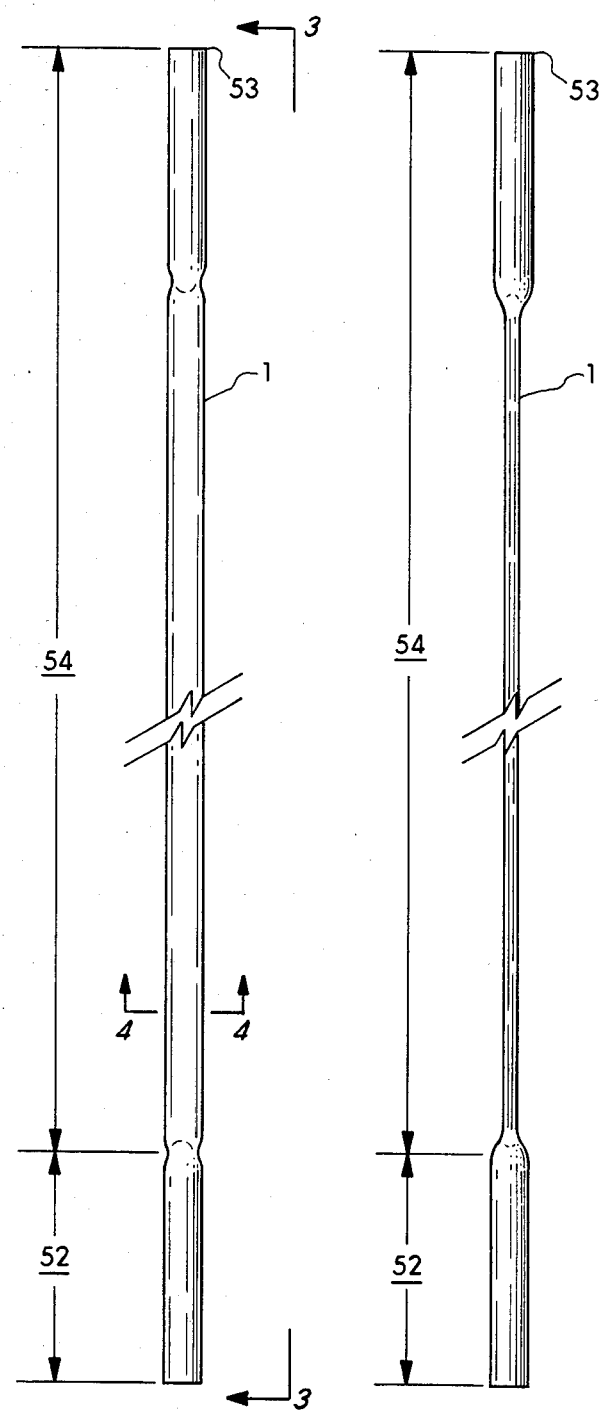
FIG. 2 is a frontal view of one embodiment of the glass tube.
FIG. 3 is a side view of the glass tube of FIG. 2.
Figure 4:
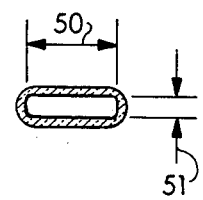
FIG. 4 is a cross-sectional view of the glass tube of FIG. 2.

An embodiment of tube 1 is shown in FIGS. 2, 3, and 4. FIGS. 2 and 3 are actual size. FIG. 4 is enlarged to a scale of 3:1. Tube 1 has an upper section 54 which is the bubble-liquid contacting portion of the tube and a lower section 52 which is the bubble-forming portion of the tube. Upper section 54 is substantially longer than lower section 52. Tube 1 is substantially rectangular in cross-section throughout except for cylindrical lower section 52 and a cylindrical portion near the top end 53 of tube 1. The cross section has an inside width 50 of 0.5 cm and depth 51 of 0.1 cm. The aspect ratio of the tube which is the width divided by depth is 5, lower section 52 of tube 1 is about 3.8 cm long and cylindrical, having an inside diameter of about 0.5 cm. Lower section 52 is flared and open to the interior of vessel 4 to enable bubble formation therein. A fitting 2 is placed over top end 53 of tube 1 to accommodate a line 27 and prevent direct fluid communication between tube 1 and vessel 4 via top 53. The portion of tube 1 near top 53 is flared in the same manner as lower section 52 solely to accommodate fitting 2.

A hollow 16-gauge needle 20 is directed into the opening of lower section 52. Needle 20 has a tip 3 which preferably penetrates into the interior of lower section 52. Alternatively tip 3 is located in vessel 4 directly below the opening. Needle 20 communicates with an external gas source 26 by a metering means 21, such as a syringe or metering pump. Metering means 21 regulates the flow of gas through needle 20 into lower section 52 and enables the formation of bubbles having constant volume. Bubble sizes may be varied using needles 20 of differing diameters.

Top end 53 of tube 1 is not open to vessel 4, but tube 1 communicates with a liquid sample source 30, containing fresh liquid samples, via a liquid sample line 29. Tube 1 also communicates with a solvent source 31, containing cleaning solvents such as heptane or toluene by means of a solvent line 28. Sample and solvent lines 28 and 29 are merged into a single line 27 which enters top end 53 of tube 1. Line 32 also merges with line 27 as an offtake to expel used liquid samples from tube 1.

A pressure maintenance means 40 is provided in fluid communication with vessel 4 via a line 44 into a pressure maintenance port 45 in vessel 4. Pressure maintenance means 40 is a reservoir containing a hydraulic fluid which maintains a preselected pressure on the liquid sample in tube 1 at the outset of the experimental runs. Reservoir 40 allows small volumes of liquid or gas to be injected into the fixed volume of vessel 4 with only small increases in pressure by maintaining a pressurized gas head 46 over the hydraulic fluid in reservoir 40. A surge valve 41 may be installed in the hydraulic fluid line 44 between reservoir 40 and vessel 4 to shut off line 44 should vessel 4 rupture. Line 44 is also connected to a pressure gauge 42 and a hydraulic fluid source 43 should it become necessary to add fluid to reservoir 40 or vessel 4. A second hydraulic fluid port 23 may be provided in vessel 4 for adding additional fluid from source 25 to vessel 4 or withdrawing fluid via line 24.

Vessel 4 is in temperature bath 5 such as a heated mineral oil to enable strict temperature control of the process. Bubble injection means 20 may also have a heating means to prevent condensation of the pressurized gas therein.

The actual materials used for vessel 4 and tube 1 may vary. However, it is critical that vessel 4 and tube 1 be transparent to allow visual observation and that vessel 4 be able to withstand the operating pressure differential across its walls. Glass is the material of choice, although transparent plastics may also be used. Further, it is preferred that all remaining wetted parts of the RBA be of stainless steel or glass.

The RBA is operated by filling the transparent vessel 4 and tube 1 with the hydraulic fluid via line 44 and/or 24. The hydraulic fluid may be the same fluid as the liquid sample, but is preferably substantially any other fluid which is inert in the gases and liquids being tested, relatively immiscible in the liquid sample at the experimental conditions, and results in an interfacial tension between it and the gas which is greater than that between the liquid sample and the gas to promote formation of sufficiently large visible bubbles. For example, water is the preferred hydraulic fluid where the gas is substantially pure $CO_2$ and the liquid sample is crude oil. Where the gas is a multicomponent mixture, it is preferable to use a hydraulic fluid in which all of the gas components are insoluble. Mercury is one such fluid which generally satisfies this requirement.

The liquid sample, i.e., oil in this case, is added to tube 1 via line 27 and displaces the water from tube 1. However, an amount of water is preferably retained in flared lower section 52 of tube 1 sufficient to immerse tip 3 of needle 20. The pressure in vessel 4 and tube 1 is adjusted to a predetermined level below the MMP by adding or removing water via line 44 and/or 24. The pressure is maintained by gas head 46 in pressure reservoir 40. The gas is a compressible gas, such as nitrogen, which is not soluble in the hydraulic fluid to a significant degree.

The bubble-forming gas is metered into needle 20 at a fixed volume to form a bubble in the water at tip 3. A preferred bubble volume enabling visibility in tube 1 of FIG. 2 is about 0.03 cubic centimeters. The bubble rises from tip 3 under its buoyant force, through the water in lower section 52, across the water-oil interface, and up through the oil column of upper section 54.

Where a tube having an elongated cross-section is used, such as in FIG. 2, the bubble maintains substantial contact with the interior wall of upper section 54, enhancing its visibility. In some cases it may be desirable to pretreat the tube walls with a chemical agent to render them oil or water wet before adding any liquids. The glass tube is preferably coated with an agent, such as DRI-FILM, a trademark of The General Electric Co., Fairfield, CT, USA, which is a transparent silicon resin solution. The agent renders the glass surface oil wet and prevents bubbles formed in the water from adhering to the glass surface of tube 1.

The shape and motion of the bubble are observed as it passes through the oil. The bubble may be photographed with a still, video or motion picture camera. Backlighting of tube 1 enhances visual observation and photography.

The gas bubble accumulates in closed line 27 after exiting upper section 54. After one or more bubbles have risen through the column of oil, the used oil sample is flushed from the 1 out lines 27 and 32 using water injected via lines 23 or 44. Tube 1 is rinsed with a solvent from source 31 via lines 28 and 27 to clean any remaining oil from the tube walls. The solvent is then flushed out through lines 27 and 32 with water and replaced by a fresh oil sample from source 30 via lines 29 and 27.

Additional runs are conducted at incrementally increased pressures according to the same procedure until the MMP is observed. The MMP is the lowest pressure at which the gas bubble exhibits characteristic multiple contact miscibility behavior. In practice runs may be continued at pressures above the observed MMP to verify the determination.

The apparatus and procedure are adaptable to pressures and temperatures which are limited only by the material limits of the apparatus. Generally the operating temperature is fixed at the anticipated temperature of the reservoir which will be gas flooded. Virtually any gas is suitable for testing according to the present invention including $CO_2$, $CH_4$, $N_2$, $C_2H_6$, $C_3H_8$, $N_2O$, $SO_2$, and blends thereof.

The mechanism by which it is believed the gas becomes miscible in a multi-component liquid, such as crude oil, is termed the multiple contact miscibility mechanism. According to this mechanism, the first oil contacted by the gas bubble in the tube is fresh oil. Mass transfer occurs across the bubble-oil interface, with light hydrocarbon components going from the oil into the gas bubble and some gas from the bubble dissolving in the oil. As the gas bubble rises upward in the oil, it contacts more fresh oil and accepts more components from the oil, changing the composition of the gas in the bubble. The actual quantity of light hydrocarbon components entering the bubble from the oil by mass transfer is a strong function of the pressure and to a lesser extent the contact time. At the MMP a sufficient quantity of components enter the bubble from the oil to render the bubble miscible in the oil.

In the present apparatus, the tube holding the oil is long enough by design to provide a sufficient contact time in most cases, even when mounted at a 90° angle from the horizontal, to dissipate the bubble in the oil at the MMP. However, should a longer contact time be required, the tube can be slanted to a smaller angle from the horizontal. As the deviation angle becomes closer to the horizontal, the buoyant force is reduced and the contact time is increased. Surprisingly, neither increased wall effects incurred by using tubes of differing cross-sectional geometry and large aspect ratios nor differences in bubble sizes produced by different needle sizes appear to significantly impact the MMP determination. The parameters of the tube geometry and bubble size are generally considerations only with respect to their effect on the visibility of the bubble in the liquid. In all cases the design and operating parameters must be selected such that the gas bubble is readily visible in the oil.

Figure 5:
FIG. 5 is a depiction of gas bubble shapes over time in a synthetic oil at varying pressures.
Figure 5:
Figure 5:
Figure 5:
Figure 5:
Figure 5:
Figure 5:
Figure 5:
Figure 5:
Figure 5:
Figure 5:
Figure 5:

FIG. 5 depicts the characteristic visible behavior of a gas bubble as the pressure approaches the MMP of the particular gas in the liquid. Each lettered series depicts a single gas bubble as it passes from the bottom to the top of the tube through the liquid sample. The gas is $CO_2$ and the liquid sample is a mole fraction mixture of 0.43 normal pentane and 0.56 normal hexadecane at a temperature around 50° C. In series A the pressure is far below the MMP, 10,550 kPa. The volume of the bubble decreases as gas transfers to the oil phase, but the entire bubble retains its initial well-defined boundary and shape as it rises through the liquid sample column. The bubble is bullet-shaped, having a nearly spherical top and a flat bottom. For long contact times, the bubble may gradually shrink to almost invisibility, but still retains its bullet shape.

In series B the pressure is at or slightly above the MMP, 10,620 kPa. The bubble retains its bullet shape when it first contacts the liquid sample. However, as it rises in the column, the flat gas-oil interface at the bottom of the bubble begins to degrade, appearing tail-like, before quickly dispersing in the liquid.

In Series C the pressure is well above MMP, 10,690 kPa. The bottom of the bubble develops tail-like features immediately on contact with the liquid sample and disperses immediately thereafter. At even higher pressures the gas bubble disperses immediately upon contact with the liquid sample.

The following examples are illustrative of the method using the apparatus of the present invention but are not to be construed as limiting the scope thereof.

EXAMPLE 1

The sight gauge and tube in the apparatus of FIGS. 1–4 are filled with water. The water is then displaced from the upper section of the tube by a recombined oil A having a bubble-point pressure of 13,620 kPa at 116° C. and a composition analysis listed below in Table 1.

TABLE 1

COMPOSITION ANALYSIS OF RECOMBINED OIL A

| Component | Mole Percent |
|---|---|
| $CO_2$ | 0.36 |
| $N_2$ | 0.10 |
| $C_1$ | 32.30 |
| $C_2$ | 4.26 |
| $C_3$ | 3.67 |
| $iC_4$ | 0.93 |
| $nC_4$ | 2.46 |
| $iC_5$ | 1.52 |
| $nC_5$ | 1.26 |
| $C_6$ | 4.69 |
| $C_7$ | 5.01 |
| $C_8$ | 6.47 |
| $C_9$ | 4.55 |
| $C_{10}$ | 3.31 |
| $C_{11}$ | 2.49 |
| $C_{12+}$ | 26.62 |

The water is pressurized to a selected pressure below the MMP and equilibrated at a selected temperature. A gas bubble is formed in the water contained in the flared lower section of the tube and propelled by buoyant force across the water-oil interface. The bubble is observed and photographed as it rises through recombined oil A in the upper section of the tube. After the bubble has passed through the tube, the used oil is flushed from the tube and the tube is washed with a heptane solvent.

A new sample of recombined oil A is placed in the tube and pressurized to an incrementally higher pressure. A gas bubble is formed at the incrementally higher pressure, but the same fixed temperature as above. The bubble is observed and photographed as it rises through recombined oil A in the tube. This procedure is repeated as many times as necessary until a bubble is first observed to exhibit characteristic multiple contact miscibility behavior. The lowest pressure at which this occurs is the MMP.

Table 2 lists the MMP's determined by the procedure above for a number of gases and gas blends in recombined oil A at different fixed temperatures.

TABLE 2

RECOMBINED OIL A

| Gas & Gas Blends | Temperature (°C.) | MMP (kPa) |
|---|---|---|
| $CO_2$ | 38 | 12570–14810 |
|  | 49 | 14320 |
|  | 60 | 16760 |
|  | 71 | 18510 |
|  | 82 | 19910 |
|  | 116 | 20610 |
| $N_2$ | 116 | 43310 |
| $CH_4$ | 116 | 39120 |
| $C_2H_6$ | 71 | 11870 |
|  | 82 | 12430 |
|  | 116 | 13620 |
| 0.13 $C_2H_6$/0.87 $CH_4$ | 116 | 35270 |
| 0.25 $C_2H_6$/0.75 $CH_4$ | 116 | 32830 |
| 0.13 $C_2H_6$/0.87 $N_2$ | 116 | >43310 |
| 0.25 $C_2H_6$/0.75 $N_2$ | 116 | >43310 |
| 0.15 $C_3H_8$/0.85 $N_2$ | 116 | >43310 |
| 0.15 $C_4H_{10}$/0.85 $N_2$ | 116 | >43310 |
| 0.25 $C_4H_{10}$/0.75 $N_2$ | 116 | >43310 |

Table 2 indicates that $C_2H_6$ has the lowest MMP of the gases tested in recombined oil A followed by $CO_2$. $CH_4$ has a relatively high MMP. The blending of $C_2H_6$ with $CH_4$ proportionally reduces the MMP of $CH_4$. $N_2$ has a still higher MMP than $CH_4$. The MMP of $N_2$ in oil A is not achieved even after blending $C_2H_6$ with $N_2$. This data has practical application for determining the most effective and economical gas which can be injected into the formation containing oil A to enhance oil recovery therefrom.

EXAMPLE 2

The MMP's of pure $CO_2$ and impure $CO_2$ in a recombined oil B at a temperature of 40° C. are determined using the apparatus and procedure of Example 1. Recombined oil B has a bubble-point pressure of 10,110 kPa at 40° C. and the stock tank oil from which recombined oil B is derived has an API specific gravity of 34.0. The impure $CO_2$ has a molar composition of 80% $CO_2$, 10% $CH_4$, 7% $N_2$ and 3% $C_2H_6$. The pure $CO_2$ is essentially 100% $CO_2$.

The MMP of pure $CO_2$ in recombined oil B using the RBA is determined to be about 12220 kPa and the MMP of the impure $CO_2$ in recombined oil B is determined to be about 17,810 kPa.

The MMP's of the same pure $CO_2$ and impure $CO_2$ gases as above are determined at 40° C. using a slim tube method. Recombined oil B' is produced from the same field as recombined oil B. The bubble-point pressure of recombined oil B' at 40° C. is 10,230 kPa.

In comparison to experiments using the RBA, the MMP of pure $CO_2$ in recombined oil B' using the slim tube method is determined to be about 12,220 kPa and the MMP of impure $CO_2$ in recombined oil B' is about 18,160 kPa. These results compare closely with the MMP results obtained with recombined oil B using the RBA. The slight differences in MMP's may be attributable to the differences in the bubble-point pressures between recombined oils B and B'.

MMP determinations in general are less precise at relatively low temperatures approaching ambient, i.e., below about 49° C., due to complex phase behavior. See Table 2. However, comparative studies of MMP's of $CO_2$ in synthetic oils at 38° C. determined by (1) the present apparatus and method; (2) the slim tube method; and (3) prediction from PVT data indicate favorable agreement between the data with acceptable error. See Table 3.

TABLE 3

COMPARISON OF MMP MEASUREMENTS OF SYNTHETIC OILS AND $CO_2$

| Synthetic Oil | Minimum Miscibility Pressure, (kPa) | | |
|---|---|---|---|
|  | RBA | PVT | Slim Tube |
| 0.675 $nC_5H_{12}$ 0.325 $nC_{16}H_{34}$ | 9020 | 8380 | — |
| 0.50 $nC_5H_{12}$ 0.50 $nC_{16}H_{34}$ | 10700 | — | 11000 |
| 0.43 $nC_5H_{12}$ 0.57 $nC_{16}H_{34}$ | 10840 | 10480 | 10480 |
| 0.18 $nC_5H_{12}$ 0.82 $nC_{16}H_{34}$ | 14050 | 12570 | — |

EXAMPLE 3

The behavior of pure $CO_2$ bubbles in $CO_2$-saturated n-decane is observed using the apparatus and procedure of Example 1. This behavior is correlated with interfacial tension (IFT) data for the bubble-decane interface which is determined independently at similar pressure and temperature conditions.

The results show that when the IFT ranges from 7.81 to 0.529 mN/m, the bubble remains nearly spherical on the top and flat on the bottom. When the IFT is about 0.1±0.02 mN/m, the bubble develops tail-like features on the bottom. When the IFT decreases to about 0.05 mN/m, the bubble disperses almost immediately upon contact with the liquid sample.

The examples presented above demonstrate the operability of the present invention. While the foregoing preferred embodiment of the invention has been described and shown, it is understood that the alternatives and modifications, such as those suggested and others, may be made thereto and follow in the scope of the invention.

We claim:

1. An apparatus for measuring the minimum miscibility pressure of a gas in a liquid comprising:
    a substantially enclosed transparent pressure vessel;
    a transparent tube having an open bottom and a closed top;
    said tube mounted such that said pressure vessel substantially encloses said tube in a substantially constant pressure environment and the interior of said tube directly fluid communicates with the interior of said vessel essentially only via said open bottom;
    a liquid feed means connected to said tube substantially above said open bottom for placing said liquid directly into said tube;
    a bubble injection means directed into said open bottom of said tube for injecting a bubble formed from said gas into said tube via said open bottom;
    a gas discharge means connected to said tube substantially above said open bottom and said bubble injection means for discharging said bubble from said tube; and
    a pressure maintenance means in fluid communication with said vessel and said tube for maintaining said substantially constant pressure environment in said vessel and tube by automatically responding to the injection of said bubble into said tube.

2. The apparatus of claim 1 wherein said tube has an upper section containing said closed top and a lower section containing said open bottom and wherein said upper section has an elongated cross-section, said lower section is flared to said open bottom, and said upper section is substantially longer than said lower section.

3. The apparatus of claim 1 wherein the longitudinal axis of said tube deviates an angle from the horizontal.

4. The apparatus of claim 1 wherein said bubble injection means comprises a hollow needle.

5. The apparatus of claim 4 wherein said needle penetrates said open bottom of said tube.

6. The apparatus of claim 2 wherein the cross section of said upper section is a rectangle.

7. The apparatus of claim 1 wherein said pressure maintenance means comprises a pressurized hydraulic fluid reservoir.

8. The apparatus of claim 3 wherein the longitudinal axis of said tube deviates about 90° from the horizontal.

9. The apparatus of claim 1 further comprising a solvent line providing fluid communication between a source of a solvent and said tube.

10. The apparatus of claim 1 wherein said liquid feed means is connected to said tube at said closed top.

11. The apparatus of claim 1 further comprising a temperature control means for controlling the temperature of said tube and contents thereof.

12. The apparatus of claim 11 wherein said temperature control means comprises a temperature bath enclosing said tube.

13. A process for determining the minimum miscibility pressure of a gas in a liquid wherein a transparent tube contains a sample of said liquid, the process comprising the steps of:
    (a) maintaining said liquid sample stationary in said tube at a predetermined substantially constant temperature and a predetermined substantially constant pressure below said minimum miscibility pressure;
    (b) forming a visible gas bubble;
    (c) discharging said gas bubble into one end of said stationary liquid sample contained in said tube while maintaining said liquid sample at said predetermined substantially constant pressure in response to said discharge of said gas bubble into said sample;
    (d) propelling said gas bubble from said one end of said stationary sample to the other end of said stationary sample such that said gas bubble continuously and visibly contacts said liquid sample;
    (e) visually observing the shape of said bubble as it is propelled through said stationary liquid sample;
    (f) increasing the pressure of said liquid sample to a predetermined substantially constant incrementally higher pressure while maintaining said sample stationary and at said substantially constant temperature and repeating steps b, c, d, and e;
    (g) repeating step f at increasing incrementally higher pressures until said gas bubble visually exhibits miscibility behavior as it is propelled through said liquid sample; and
    (h) determining said minimum miscibility pressure to be the lowest incrementally higher pressure at which said bubble visually exhibits miscibility behavior.

14. The process of claim 13 wherein said pressure below the lowest minimum miscibility pressure and said incrementally higher pressure are maintained on said liquid sample by means of a hydraulic fluid automatically responsive to said discharge of said gas bubble into said sample.

15. The process of claim 14 wherein said tube has an upper section and a lower section and wherein said upper section contains said liquid sample and said lower section contains said hydraulic fluid.

16. The process of claim 14 wherein said bubble is formed in said hydraulic fluid.

17. The process of claim 16 wherein said bubble is formed in said lower section of said tube.

18. The process of claim 13 wherein said liquid sample is a liquid hydrocarbon.

19. The process of claim 18 wherein said liquid sample is a crude oil.

20. The process of claim 13 wherein said gas is selected from the group consisting of $CO_2$, $CH_4$, $C_2H_6$, $C_3H_8$, $N_2O$, $SO_2$, $N_2$ and mixtures thereof.

21. The process of claim 20 wherein said gas is $CO_2$.

22. The process of claim 14 wherein the interfacial tension between said hydraulic fluid and said gas is greater than the interfacial tension between said liquid sample and said gas.

23. The process of claim 14 wherein said hydraulic fluid is water.

24. The process of claim 14 wherein said pressure below said minimum miscibility pressure and said incrementally higher pressure is maintained by a pressurized gas head on said hydraulic fluid.

25. The process of claim 13 wherein said bubble is propelled through said liquid by a buoyant force on said bubble.

26. The process of claim 25 wherein the longitudinal axis of said tube is aligned at an angle deviating from the horizontal.

27. The process of claim 26 wherein said angle is selected to determine the time that said gas contacts said liquid.

28. The process of claim 26 wherein the longitudinal axis of said tube is aligned 90° from the horizontal.

29. The process of claim 15 wherein said upper section of said tube has an elongated cross-section and said gas bubble substantially and continuously contacts an interior wall of said upper section.

30. The process of claim 13 further comprising expelling said liquid sample from said tube after said gas contacts said liquid and charging a fresh liquid sample to said tube having substantially the same composition as said liquid sample before said gas contacts said liquid.

* * * * *